United States Patent [19]

Langen et al.

[11] Patent Number: 4,944,958
[45] Date of Patent: Jul. 31, 1990

[54] METHOD OF MANUFACTURING A COHESIVE BANDAGE

[75] Inventors: Gunter Langen, Wolfstein; Harald Jung, Kreimbach-Kaulbach, both of Fed. Rep. of Germany

[73] Assignee: Karl Otto Braun KG, Wolfstein, Fed. Rep. of Germany

[21] Appl. No.: 345,409

[22] Filed: Apr. 28, 1989

Related U.S. Application Data

[62] Division of Ser. No. 92,084, Sep. 2, 1987.

[30] Foreign Application Priority Data

Sep. 5, 1986 [EP] European Pat. Off. ............ 86112283

[51] Int. Cl.⁵ ............................................. A01N 1/02
[52] U.S. Cl. ........................................ 427/2; 128/157; 128/169; 523/111
[58] Field of Search ............... 128/156, 157, 169, 170, 128/89 R, 90, 80 R; 427/2; 2/22; 523/111, 118; 428/481

[56] References Cited

U.S. PATENT DOCUMENTS 2,238,878  4/1941  Baitz et al. .......................... 128/156
3,575,782  4/1971  Hansen ................................ 128/156
4,366,814  1/1983  Riedel ................................. 128/169
4,800,872  1/1989  Buese et al. ........................ 128/89 R

FOREIGN PATENT DOCUMENTS 0557323  11/1943  United Kingdom ............... 523/111
1297280  11/1972  United Kingdom .
1442648   7/1976  United Kingdom .

Primary Examiner—Randall L. Green
Assistant Examiner—Paul Prebilic

[57] ABSTRACT

A method of manufacturing a cohesive bandage comprising the steps of providing at least one layer of woven fabric and applying a coating containing polybutylacrylate ester and alkylphenyl polyethylene glycol to at least one fabric face is disclosed. In one embodiment, the coating is applied by an airless method, microselectively in statistical distribution where the quantity of coating is controlled by pump pressure. Alternatively, an aqueous dispersion of polybutyl acrylate ester and carboxymethyl cellulose is microselectively and cohesively coated on both sides of the fabric by screen printing to produce a regular dot pattern on both faces of the fabric.

5 Claims, 2 Drawing Sheets

METHOD OF MANUFACTURING A COHESIVE BANDAGE

CROSS REFERENCE TO RELATED APPLICATION

The subject application is a division of Ser. No. 092,084, filed Sept. 2, 1987 and claims priority to the European patent application No. 86112283.6.

BACKGROUND OF THE INVENTION

The present invention relates to a cohesive bandage, the individual layers or bandage application turns of which adhere only to one another and not to the skin, hair and garments, said bandage being manufactured from a woven material, finely or coarsely knitted fabric or from fleece for immobilizing, supporting, compression or relieving bandages for medical purposes as well as to a method for the manufacture of said bandage.

In the case of cohesive bandages, when bandaging injured parts of the body, solely the overlapping bandage application turns adhere to one another; a sticking together with the skin or hair does not take place. Also, when the bandage is removed, no traces of the adhesive substance adhere to the skin; in contrast to adhesively coated bandages it is possible to remove the bandage painlessly. According to the DE-A-581 676, non-coagulated natural rubber with the addition of anti-aging agents not specified in detail is employed as raw material with cohesive adhesive properties.

According to the DE-A-688 430, a gauze or muslin bandage coated with natural rubber in the dip coating method is known, wherein the proteins present in the natural latex, subsequent to the coating, should be removable by means of a coagulation process involving the use of acetic acid and subsequent washing, whereby an improved shelf life and a non-discoloration of the bandages impregnated in this manner is supposed to be achieved, said advantages being attributed to the absence of the proteins otherwise present in the rubber.

However, the bandages manufactured according to the DE-A-688 430 are subject to the known shortcomings of bandages coated in the dipping process, such as extensive loss of the absorptive capacity and permeability to air as well as of the plasticity and the textile nature. Over and above this, following numerous tests it has become evident that the use of natural rubber without the addition of anti-aging agents holds out no prospects of attaining an adequate storage life.

According to the U.S. Pat. No. 2,238,878, methods for the cohesive structuring of muslin, cheese cloth, butter muslin and similar textiles are known, in conformity with which small fragments of natural rubber are applied to one or both surfaces of the same. In such cases it is intended to maintain the relatively large apertures in the fabric in order to obtain an improved permeability to air. The natural latex dispersion employed in this method is not specified in greater detail as to its composition; in particular no data are furnished regarding the admixture of anti-aging agents and other ancillary agents, so that it has to be assumed that bandages of this type do possess the known drawbacks such as a strong tendency to discoloration, loss of the cohesiveness and becoming smeary due to the effects of aging or of temperature influences.

The U.S. Pat. No. 3,575,782 describes a method for the manufacture of elastic wrapping materials fabricated from fibrous fabrics and highly elastic rubber or polyurethane threads while use is being made of coherent binding agents. A number of pre-stretched rubber threads are supplied to the two non-bound webs of fleece material consisting e.g. of polyester fibers in such a way that these come to lie distortedly between the two layers of fleece material. By the employment of coherent binding agents as, for instance, natural rubber or synthetic polymers, the pre-stretched rubber threads in the laminate are strengthened in such a manner that a cohesive, elastic laminate is produced during the subsequent drying and shrinking process. The rubber-like binding agents of either a natural or synthetic kind give rise to a weakly sticky, adhesive feel, as a result of which a sticking together with skin, hair or garments is hardly given, it is true, however, due to the poor adhesive properties, bandages of this type possess an unpleasant greasy or smeary feel. If this greasy or smeary feel is lost due to e.g. a sterilization operation, then this is also connected with the loss of the cohesiveness. The fleece material laminate bandages manufactured according to this method possess, on account of their construction, a binding agent proportion of at least 50%, so that these bandages do not possess the textile nature desired in the sphere of bandages, but rather exhibit the behavior of a rubber band, which results from the circumstance that the incorporated polyurethane or rubber threads lead to constrictions and varying surface pressure. Moreover, the loss of the permeability to air has to be regarded as a further serious shortcoming.

According to the GB-A-1,297,280, a self-adhesive, non-woven, air-permeable fleece material fabricated from rayon fibers is known. The cohesive coating of the fibrous fleece material is effected by means of a mixture of natural latex and synthetic resin latices, the proportion of synthetic resin latex being by far greater than the proportion of natural rubber. However, in this case, both components serve primarily to strengthen the fleece material. By means of the partial coating with adhesive substance it is intended to achieve an adequate strength coupled with a good permeability to air, the adhesive properties are brought about in dependence of the respective type of mixture used.

The DE-A-491 205 describes a method for the manufacture of cohesive, elastic compression bandages which, due to the partial, striated coating with the adhesive are permeable to both air and water vapor. In the bandages or dressings manufactured according to this method, the strip of fabric is conducted between tangentially disposed coating rollers which are provided with recesses. The desired partial coating is achieved by the recesses in the fluted rollers. As adhesive compound, a mixture of dry rubber latex, potassium oleate, anti-aging agent and silicone oil is used. Prior to the coating operation, the adhesive used has to be disposed as solid matter in a low-boiling solvent, e.g. benzene, which is confirmed further by the low drying temperature of 35° C. which is used.

The DE-A-29 12 129 describes a method for the manufacture of air-permeable, cohesive, highly elastic bandages, the cohesiveness being achieved by a superfine dispersion of latex particles on the fiber surface. The adhesive used is exclusively a stabilized, aqueous rubber dispersion.

As opposed to the bandages coated with adhesive compounds which adhere to almost all articles of daily use and materials and which possess a permanent, aggressive tackiness, and purely cohesive adhesive effect is distinguished in that the adhesive forces are effective solely within the adhesive substance and bring about the internal cohesion of the substance. Consequently, a bandage coated with a cohesive substance only adheres to itself, i.e. layer to layer or bandage application turn to bandage application turn, but not to foreign surfaces such as skin, hair or garments. This cohesive adhesive behavior was up till now chiefly regulated by employing non-vulcanized rubber based on natural latex, whereby appropriate cohesive bandages are produced according to the dipping, lick roll or spraying process while use is made of a, in most cases, 60% latex dispersion (centrifuge latex). In this case it is inevitable to stabilize the latex with ammonia prior to the processing which, due to the negative ionogeity, limits the possibility of mixing with other suitable synthetic polymers or anti-aging agents. Over and above this, it is necessary when employing natural latex, to add antioxidants in the form of special organic compounds, as, for example, sterically inhibited phenols in order to achieve an adequate storage life (aging resistance) and to avoid embrittlement phenomena or desiccation processes. The cohesive adhesive behavior can be varied by mixing with suitable synthetic polymers in such a way that more or less strongly pronounced adhesive properties exist. Chiefly rubber-like latices, as e.g. polyisoprene, polybutadiene, butadiene-styrene, acrylonitrile, butadiene copolymers are used as synthetic polymers.

When employing natural latex as cohesive adhesive, a number of drawbacks will have to be accepted. Despite the addition of antioxidants the storage life is severely limited.

On account of the double bond still present in the rubber molecule, a marked reactivity vis-à-vis atmospheric oxygen exists, as a consequence of which the oxidation processes result in a becoming greasy or smeary or in the embrittlement of the rubber. These effects are accelerated further by the effects of light, heat, radiation as well as of certain chemicals such as heavy metals and the like, so that the natural rubber still has to be regarded as being decidedly sensitive to oxidation. The addition of anti-aging agents entails a number of further drawbacks. Thus various anti-aging agents lead to allergies and dermal irritations in different persons and cannot in each case be looked upon as being completely harmless from a toxicological point of view. Furthermore, some of these antioxidants tend to discoloration, which results in a yellowing or pink coloration of the entire latex substance, the bandage thus becoming unsightly. This effect is partially intensified still further by the packing materials and by the atmosphere. It is known, furthermore, that high temperatures are injurious to the rubber adhesive substance, so that difficulties will arise when appropriate bandages are subjected to heat or steam sterilization. Also the use of other sterilization methods, as, for instance, sterilizations effected with the aid of gamma or beta rays meet with great difficulties since the rubber molecules are partially cracked by the high-energy radiation. The bandages become unsightly and useless (yellowing, greasy/smeary feel, embrittlement, loss of adhesion).

In order to circumvent the known drawbacks of the natural rubber and its mixing with rubber-like synthetic polymers, there has ben no lack of attempts in the past aimed at eliminating these product shortcomings. Thus, by way of example, a search was made for improved antioxidants and better packing materials, without that a sweeping success was achieved.

SUMMARY OF THE INVENTION

The invention solves the technical problem of providing a sterilizable, aging-resistant, cohesive bandage which, in its property profile regarding the permeability to air and water vapor, absorptive capacity, elastic behavior, wash-fastness, storage life as well as in a toxicological respect, is superior to the known types of cohesive bandages and, furthermore, of finding suitable synthetic substitute products for natural rubber which possess a likewise purely cohesive adhesive behavior, can be employed in the sphere of bandages and which permit the manufacture of cohesive bandages which, however, do not comprise the shortcomings of the natural rubber described in the foregoing.

This problem is solved by a cohesive bandage of the kind described at the beginning which, according to the invention, consists of an adhesive substance applied to one side or to both sides of the fabric that is produced from an acrylic resin dispersion of the group of the crosslinked and non-crosslinked polyacrylate esters, by preference a polybutylacrylate ester, it being possible for a wetting agent and/or foam stabilizers being added to the acrylic resin dispersion.

It has surprisingly become apparent that certain defined derivates of the class of the acrylic resin dispersions possess the desired purely cohesive adhesive behavior. This is the group of the crosslinked or non-crosslinked polyacrylate esters, preferably polybutylacrylate esters, which are available in the form of aqueous dispersions corresponding to natural rubber. These dispersions are applied to the textile substrate in accordance with various methods still to be described afterwards, so that a product is obtained corresponding to the known cohesive adhesive bandage but possessing improved properties. The dispersions can be processed in a pure form, the addition of anti-aging agents or antioxidant products is dropped so that the allergies occurring over and over again when they are used are precluded. The discolorations occurring time and again when rubber is used due to the presence of antioxidants do not happen when the acrylic esters are employed. In particular the attempt to create a cohesive bandage which can be sterilized with the aid of gas, steam, heat and radiation has been crowned with success for the first time. It has become possible hereby to use cohesive bandages in the operating theater area which have already been sterilized without that the storage period is of any consequence.

According to a further feature of the invention the adhesive substance is composed of 1,000 g crosslinked polybutylacrylate ester in the form of a 50% aqueous dispersion.
2 g alkylphencyl polyethylene glycol as wetting agent and of
10 g acrylic resin size as foam stabilizer.

Furthermore, it is also possible for the adhesive substance to be composed of 1,000 g non-crosslinked polypropylacrylate ester in the form of a 60% aqueous dispersion.

Moreover, the invention provides an adhesive substance composed of 100 parts non-crosslinked polybutylacrylate ester in the form of a 50% aqueous dispersion and of
1 part carboxymethyl cellulose.

The method for the manufacture of the cohesive bandage, the individual layers or bandage application turns of which only adhere to one another and not to the skin, hair or garments, fabricated from a woven material, finely or coarsely knitted fabric or fleece for immobilizing, compression, supporting and relieving bandages for medical purposes consists in that the adhesive substance produced from an acrylic resin dispersion, in particular from a crosslinked or non-crosslinked polyacrylate ester or a polybutylacrylate ester with or without the addition of a wetting agent and/or of foam stabilizers, is applied to one side or to both sides of the woven material, the finely or coarsely knitted fabric or of the fleece of the bandage.

The method consists moreover in that the adhesive substance produced from a foamed acrylic resin dispersion composed of
1,000 g crosslinked polybutylacrylate ester in the form of a 50% aqueous dispersion, of
2 g alkylphenyl polyethylene glycol as wetting agent and of
10 g acrylic resin size as foam stabilizer.

Moreover, the adhesive substance may also be composed of 1,000 g non-crosslinked polypropyl acrylate ester in the form of a 60% aqueous dispersion.

In addition, the invention provides an adhesive substance which is composed of
100 parts non-crosslinked polybutyl acrylate ester in the form of a 50% aqueous dispersion and of
1 part carboxymethyl cellulose.

The method for the manufacture of the cohesive bandage, the individual layers or bandage application turns of which only adhere to one another and not to the skin, hair or garments, fabricated from a woven material, a finely or coarsely knitted fabric or a fleece for immobilizing, supporting, compression and relieving bandages for medical purposes, consists in that the adhesive substance is produced from an acrylic resin dispersion, in particular from a crosslinked or non-crosslinked polyacrylate ester or a polybutylacrylate ester with or without the addition of a wetting agent and/or foam stabilizers, is applied to one side or to both sides of the woven material, the finely or coarsely knitted fabric or to the fleece of the bandage.

The method further consists in that the adhesive substance produced from a foamed acrylic resin dispersion composed of
1,000 g crosslinked polybutylacrylate ester in the form of a 50% aqueous dispersion of
2 g alkylphenyl polyethylene glycol ether as wetting agent and of
10 g acrylic resin size as foam stabilizer
is applied with the aid of an on-roll coater in even distribution to one of the two surfaces of the flat-shaped textile structure consisting of warp and weft or of warp in the form of finely or coarsely knitted fabric or of a fleece, wherein the substance composed of
1,000 g crosslinked polybutylacrylate ester in the form of a 50% aqueous dispersion, of
2 g alkylphenyl polyethylene glycol as wetting agent and of
10 g acrylic resin size as foam stabilizer
is foamed in a foam mixer at a ratio of 1:5 at a foam weight of 200 g/liter and the roll nip height is set in such a way that 20 g foam/m² are applied unilaterally to the woven material, the finely or coarsely knitted fabric or to the fleece and, subsequently, the woven material, the finely or coarsely knitted fabric or the fleece is dried at 130° C., as a consequence of which the foam disintegrates and a complete, microporous surface covering is obtained, it then being possible to also coat the yet uncoated reverse of the flat-shaped textile structure in a like manner.

Furthermore the invention provides a method, according to which a woven material, a finely or coarsely knitted fabric or a fleece possessing a weight per unit area of approximately 90 g/m², in particular a longitudinally elastic immobilizing bandage is, is coated bilaterally with approximately 8 g/m²/side of 100 g non-crosslinked polypropylacrylate ester in the form of an undiluted 60% aqueous dispersion in accordance with the aerosol method or by atomization in accordance with the airless method microselectively in statistical distribution, in which method the quantity of coating is selected via the pump pressure and the capacity in such a way that, per fabric side, a quantity of coating of 8 to 10 g/m² is applied.

A further method consists in that a woven material, a finely or coarsely knitted fabric or a fleece possessing a weight per unit area of approximately 350 g/m², in particular a longitudinally elastic compression bandage with permanently elastic polyurethane threads, is coated microselectively and cohesively on both sides with approximately 15 g/m²/side with a substance composed of
100 parts non-crosslinked polybutylacrylate ester in the form of a 55% aqueous dispersion and of
1 part carboxymethyl cellulose
with the aid of screen printing, by means of which the concentrated aqueous acrylic resin dispersion is printed while use is made of a 40 mesh template having a perforated pattern structure, onto the web of woven material, the finely or coarsely knitted fabric or the fleece, so that a regular pattern of dots is produced on the surface of the flat-shaped textile structure, while subsequent to the drying of the unilaterally coated web of fabric, the reverse of the fabric is coated in a like manner with the acrylic resin dispersion composed of
100 parts non-crosslinked polybutylacrylate ester in the form of a 55% aqueous dispersion and of
1 part carboxymethyl cellulose.

The product advantages achieved with the cohesive bandage are to be ascribed to the insensitivity to and the resistance of the acrylate esters vis-à-vis high-energy gamma or beta rays, light, heat, steam or ethylene oxide. It has become apparent, moreover, that compression bandages, cohesively structured with acrylate esters, possess a distinctly improved wash-fastness, so that a repeated use is possible.

TABLE I

| Adhesive Substance | Rubber | Recipe per Example 1 | Recipe per Example 2 |
|---|---|---|---|
| Coating quantity dry | 20 g/m² | 20 g/m² | 16 g/m² |
| Adhesion | 70 cN/cm | 78 cN/cm | 38 cN/cm |
| Adhesion after 3 yrs. aging | 60 cN/cm | 77 cN/cm | 40 cN/cm |
| Adhesion after 6 yrs. aging | 31 cN/cm | 75 cN/cm | 38 cN/cm |
| Aging Test (Storage Life) | 5 years | 15 years | 15 years |
| Wash-Fastness | 1 × | 5 × | 7 × |
| Steam Sterilization | +− | + | + |
| Gas Sterilization | + | + | + |
| Heat Sterilization | − | + | + |
| Radiation Sterilization | − | + | + |

+ = possible
− = not possible

The coating quantity dry is determined via the difference of the weights per unit area of the coated and the uncoated supporting textile fabric.

By adhesion is understood that force which is required for the separation of two cohesive bandage sections adhering to one another, related to a length of 10 cm and a width of 1 cm.

For carrying out the measuring operation the bandage is folded to a length of 10 cm and subsequently rolled together with a roller having a temperature of 37° C. by 45 rolling motions within one minute. Following this, the ends of the bandage are clamped into a strength-elongation testing machine and drawn apart until the surfaces adhering to one another are completely separated. By integration via the strength-elongation curve it will be possible to calculate the mean adhesion within the unit cN/cm via the adhesion function. Corresponding values of the adhesion are determined after artificial aging of the cohesive bandages. The artificial aging is effected in conformity with the German standard DIN 53 896, Testing of Textiles "Artificial Aging by Elevated Temperatures."

The bandages are then stored at 70° C. for several days in the warming cabinet. According to the formula $$\frac{a-1}{2} = X$$

it is possible to determine the duration of the simulated aging X in years from the number of the storage day a. For testing the wash-fastness, the cohesive bandages are treated for 30 minutes at 60° C. with 5 g/l full-strength detergent at a bath ratio of 1:50.

The requirements for the sterilization methods listed in Table I are drawn up below:

| Steam Sterilization | Saturated, confined water vapor | |
|---|---|---|
| | Temperature | 134° C. |
| | Duration | at least 10 min |
| Heat Sterilization | Hot Air | |
| | Temperature | 180° C. |
| | Duration | 30 min |
| Gas Sterilization | Ethylene Oxide | |
| | Pressure | 70 Torr |
| | Duration | 90 min |
| Radiation Sterilization | γ-Rays | |
| | Dose | 2.5 Mrad |

In principle a cohesive bandage of the type described is suitable depending on the substrate forming the basis (woven material, finely or coarsely knitted fabric, fleece), for use as an immobilizing, compression, supporting and relieving bandage.

The bandages and dressings manufactured with the use of acrylic resin dispersions, on account of their resistance to the known sterilization methods, are particularly suited for direct application in the sterile area. It is hereby possible to apply, taken directly from an appropriate packing, a sterile bandage for the most varied applications within the field of dressing wounds, immobilizing bandages, compression bandages, supporting bandages and relieving bandages.

The sterilized bandages of the form and structure according to the invention can be stored for years in a packed state in hospitals, ambulances, pharmacies, first aid stations and even in first aid boxes without any impairment of the condition and of the utilization properties, in particular of the cohesive adhesive behavior and of the optical appearance taking place.

Even when stored at drastically elevated temperatures, as e.g. in tropical countries or, during a spell of great heat, in the trunk compartment of an automobile, the utilization properties of such a bandage are not detrimentally affected in any way whatever.

Depending on the desired cohesive effect and further utilization properties such as permeability to air, permeability to water vapor, absorptive capacity, elastic behavior and adhesion, various application techniques are available with the aid of which a complete or partial coating can be achieved.

The invention is explained with the aid of the following examples:

EXAMPLE 1

An elastic cotton compression bandage of the ideal bandage type as per German standard DIN 61 632 is coated by an on-roll coater with the following acrylic resin dispersion:

1,000 g crosslinked polybutylacrylate ether (50% aqueous dispersion)

2 alkylphenyl polyethylene glycol ether (wetting agent)

10 g acrylic resin size (foam stabilizer)

The substance is foamed in a foam mixer at a ratio of 1:5 (foam weight 200 g/liter).

The nip height of the on-roll coater is set in such a way that 20 g foam/m² fabric is unilaterally applied. The drying is effected at 130° C., as a consequence of which the foam disintegrates and allows a complete microporous surface covering to be produced. The coating of the fabric reverse is carried out analogously in a second operation. A fabric coated in this manner possesses the following physical-technical data:

TABLE II

| | uncoated | coated per Example 1 | coated per Example 1 and radiation sterilization of 2.5 Mrad. |
|---|---|---|---|
| m² weight stretched | 145 g | 155 g | 155 g |
| Elasticity | 100% | 90% | 90% |
| Permeability to air* | 800 l/m² sec | 580 l/m² sec | 570 l/m² sec |
| Adhesion | / | 78 cN/cm | 74 cN/cm |
| Coating qty/m² | / | 20 g solid matter | 20 g solid matter |

+ as per DIN 53 887

EXAMPLE 2

A longitudinally elastic immobilization bandage having a weight per unit area of approximately 90 g/m² is microselectively coated on both sides according to the aerosol method with approximately 8 g/m²/side.

Recipe 1,000 g non-crosslinked polyacrylate propyl ester (60% aqueous dispersion)

The aqueous dispersion is atomized undiluted according to the airless method and applied microselectively to the web of the fabric in statistical distribution. The quantity of the coating is selected via the pump pressure and capacity in such a way that, per fabric side, a coating quantity of 8–10 g/m² is applied. This method has the advantage that the elastic behavior is hardly affected in a negative manner.

TABLE III

|  | uncoated | coated per Example 2 | coated per Example 2 and steam-sterilized at 134° C. for at least 5 min |
| --- | --- | --- | --- |
| m² weight stretched | 30 g | 33 g | 33 g |
| Elasticity | 200% | 180% | 180% |
| Permeability to air* | 6000 l/m² sec | 5800 l/m² sec | 5800 l/m² sec |
| Adhesion | / | 38 cN/cm | 40 cN/cm |
| Coating qty./m² | / | 10.5 g solid matter | 10 g solid matter |

*per DIN 53 887

Microselective application per screen printing.

A longitudinally elastic compression bandage with permanently elastic polyurethane threads and possessing a weight per unit area of approximately 350 g/m² is coated microselectively and cohesively on both sides with approximately 15 g/m²/side dispersion by means of screen printing.

Recipe 100 parts non-crosslinked polybutylacrylate ester (55% aqueous dispersion)
1 part carboxymethyl cellulose The thickened aqueous acrylic resin dispersion is printed onto the web of the fabric while use is made of a 25-mesh template (i.e. 25 perforations per linear inch) having a perforated pattern structure, so that a regular pattern of dots is produced on the web of the fabric. Subsequent to the drying of the coated web of the fabric, the reverse of the fabric is coated with the described acrylic resin dispersion.

TABLE IV

|  | uncoated | coated per Example 3 | coated per Example 3 and sterilized by ethylene oxide |
| --- | --- | --- | --- |
| m² weight stretched | 165 g | 175 g | 175 g |
| Elasticity | 100% | 90% | 90% |
| Permeability to air* | 650 l/m² sec | 520 l/m² sec | 530 l/m² sec |
| Adhesion | / | 97 cN/cm | 108 cN/cm |
| Coating qty./m² | / | 16 g solid matter | 16 g solid matter |

*per DIN 53 887

It is of course possible, depending on the desired surface structure or coating patterns, to apply the acrylic resin dispersion according to the screen printing method by utilizing different templates. In this way it is possible to apply complete coating, partial coatings in accordance with a regular or irregular statistical pattern of dots, geometric figures (stripes, lattices) to the surface of the fabric.

In a like manner it is possible to apply a foamed acrylic resin dispersion in lieu of a printing paste, analogous to Example 1, according to the screen printing method. For the person skilled in the art it is possible to apply the described acrylic resin dispersions by means of further, known application methods such as, for instance, the lick-roll process, the dipping method or the rotational squirting method in order to obtain bandages which possess identical or analogous properties.

BRIEF DESCRIPTION OF THE DRAWINGS

In the following the subject matter of the invention is explained in the drawings.

DETAILED DESCRIPTION OF THE PREFERRED EMBODIMENTS

Figure 1:
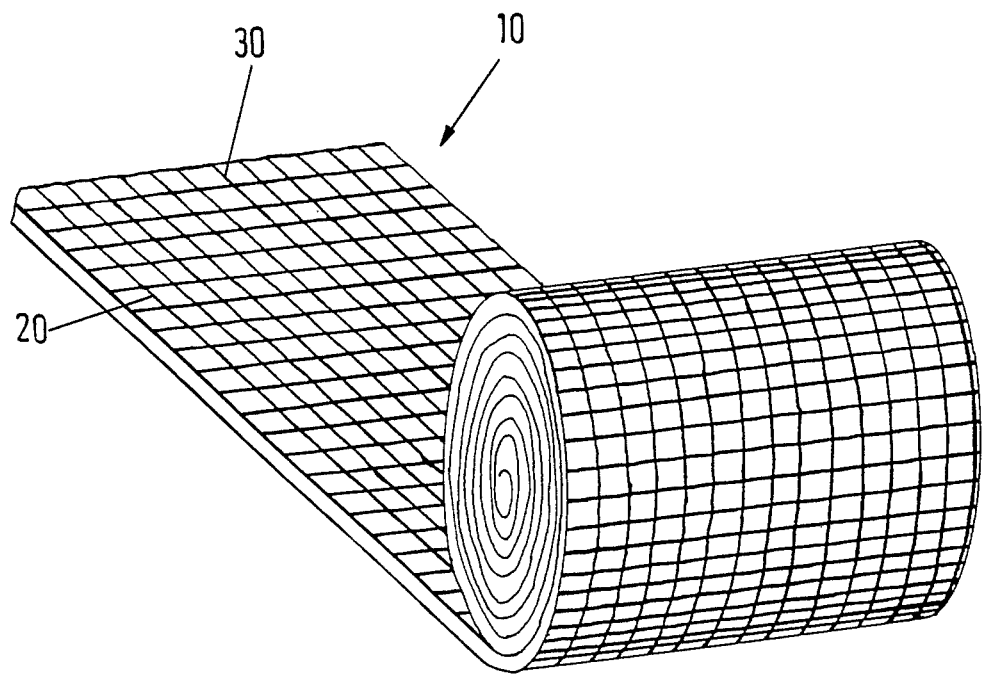
FIG. 1 shows in a diagrammatical view a bandage fabricated from bandage material, partly in a rolled-up state.
Figure 2:
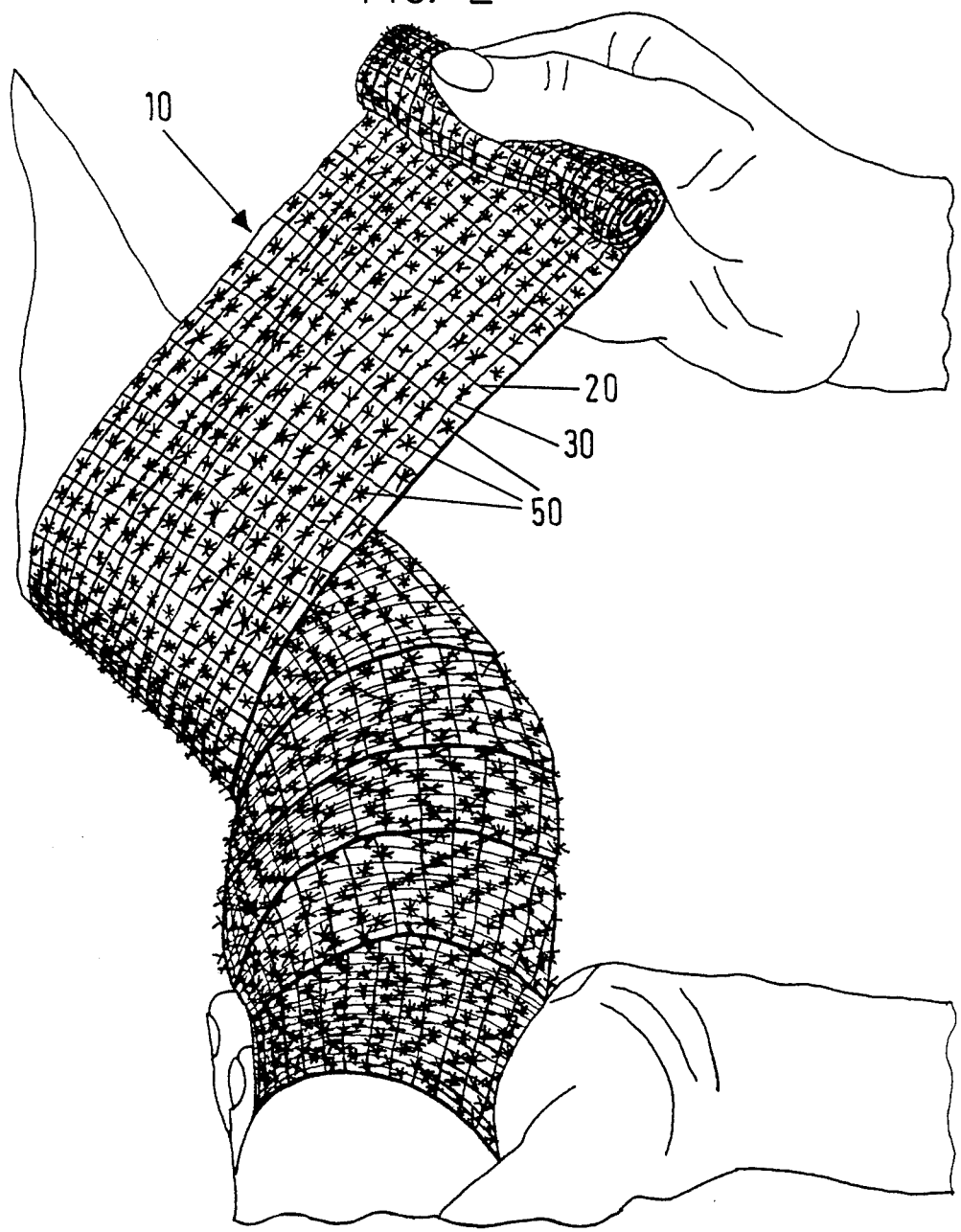
FIG. 2 shows the utilization of the adhesively structured bandage as supporting bandage on the forearm or elbow.

The bandage consisting of a flat-shaped fabric structure 10 and fabricated from bandage material possesses weft threads 20 and warp threads 30. On both sides of the unencumbered surfaces of the weft and the warp threads 20,30, the cohesive adhesive substance is applied with the aid of the screen printing method in accordance with a lattice pattern, the adhesive substance areas being indicated at 50 (FIG. 2). The bandage layers adhere solely at those points at which the bandage applications turns come to lie on top of one another. In those cases where this might prove necessary, it is also possible for the adhesive substance to be applied to one side of the flat-shaped fabric structure 10 only.

What is claimed is:

1. A Method of manufacturing a bandage comprising the following steps:
   providing a least one layer of woven fabric,
   applying a coating to at least one face of the fabric,
   said coating including an adhesive substance formed from a foamed aqueous dispersion of 50% one thousand parts polybutylacrylate ester, and two parts alkylphenyl polyethylene glycol, and ten parts stabilizer,
   adding to said dispersion a wetting agent and foam stabilizer, said coating being applied by atomization according to an airless method micro-selectively in statistical distribution wherein the quantity of coating is selected by a pump pressure in such a capacity that per fabric side the quantity of coating is 8–10 grams per square meter.

2. A method according to claim 1 wherein said woven fabric comprises a longitudinally elastic immobilizing bandage, and wherein the coating is provided bilaterally to both faces of the fabric in a sequential fashion.

3. A method for the manufacture of a bandage comprising the following steps:
   providing at least one layer of woven fabric,
   applying a coating to at least one face of the fabric, said coating including an adhesive substance formed from a foamed aqueous dispersion of 60% one thousand parts non-crosslinked polybutylacrylate ester and one part carboxymethyl cellulose, said bandage material comprising an elastic compression bandage formed with permanently elastic polyurethane threads and said applying step including micro-selectively and cohesively coating both sides of said fabric with the aid of screen printing with a 40 mesh template having a perforated pattern structure so that a regular dot pattern is produced on both faces of the fabric.

4. A method according to claim 3 wherein the fabric has a weight permit area of 350 grams per square meter and wherein the coating has a weight of approximately 15 grams per square meters on each face of the fabric.

5. The method according to claim 4 wherein the faces of the fabric are coated sequentially, one side being allowed to dry prior to application of a coating to the opposite or face of the fabric.

* * * * *